(12) United States Patent
Asselin et al.

(10) Patent No.: US 8,979,832 B2
(45) Date of Patent: Mar. 17, 2015

(54) CUTTING DEVICE AND RELATED METHODS OF USE

(75) Inventors: William Asselin, Lunenburg, MA (US); Nareak Douk, Lowell, MA (US); Troy Gardner, Carmel, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 301 days.

(21) Appl. No.: 13/570,861

(22) Filed: Aug. 9, 2012

(65) Prior Publication Data

US 2013/0041359 A1    Feb. 14, 2013

Related U.S. Application Data (60) Provisional application No. 61/521,844, filed on Aug. 10, 2011.

(51) Int. Cl.
*A61B 18/04* (2006.01)
*A61B 17/3205* (2006.01)
*A61B 17/221* (2006.01)

(52) U.S. Cl.
CPC ......... *A61B 17/32053* (2013.01); *A61B 17/221* (2013.01)
USPC ....................................................... 606/27

(58) Field of Classification Search
CPC .................... A61B 17/3205; A61B 17/32053; A61B 17/32056; A61B 17/221; A61B 2017/00349; A61B 2017/00353; A61B 2017/00358; A61B 2017/22031; A61B 2017/22034; A61B 2017/22035; A61B 2017/221
USPC ........................................................ 606/27
See application file for complete search history.

(56) References Cited

U.S. PATENT DOCUMENTS

| 4,311,143 A | 1/1982 | Komiya |
| 4,486,680 A | 12/1984 | Bonnet et al. |
| 5,197,968 A | 3/1993 | Clement |
| 5,397,320 A | 3/1995 | Essig et al. |
| 5,904,690 A * | 5/1999 | Middleman et al. .......... 606/113 |
| 6,015,381 A | 1/2000 | Ouchi |
| 6,099,534 A | 8/2000 | Bates et al. |
| 6,152,932 A | 11/2000 | Ternström |
| 6,156,043 A | 12/2000 | Krahn |
| 6,190,394 B1 | 2/2001 | Lind et al. |
| 6,203,552 B1 | 3/2001 | Bagley et al. |
| 6,221,039 B1 | 4/2001 | Durgin et al. |
| 6,368,328 B1 | 4/2002 | Chu et al. |
| 6,537,273 B1 | 3/2003 | Sosiak et al. |
| 6,833,000 B2 | 12/2004 | Levinson |

(Continued)

FOREIGN PATENT DOCUMENTS

WO    WO 03/097153 A1    11/2003

OTHER PUBLICATIONS

International Search Report for International Patent Application No. PCT/US2012/050123 dated Nov. 7, 2012, 5 pages.

*Primary Examiner* — Robert N Wieland
(74) *Attorney, Agent, or Firm* — Bookoff McAndrews, PLLC (57) ABSTRACT

A device and related methods of use are provided for the capture and removal of various unwanted objects present within the body's anatomical lumens. In an embodiment of the present disclosure, the device includes a sheath, a cutting device, an elongate member, and a retrieval assembly connected to the elongate member and retractable within and extendable from a lumen extending through the sheath and cutting device.

17 Claims, 10 Drawing Sheets

(56) References Cited

U.S. PATENT DOCUMENTS

| | | |
|---|---|---|
| 7,018,385 B2 | 3/2006 | Bates et al. |
| 7,229,418 B2 | 6/2007 | Burbank et al. |
| 7,291,146 B2 | 11/2007 | Steinke et al. |
| 2002/0087046 A1 | 7/2002 | Sullivan et al. |
| 2007/0219549 A1 | 9/2007 | Marshall et al. |
| 2007/0238177 A1* | 10/2007 | Laham et al. ............. 435/395 |
| 2008/0058673 A1 | 3/2008 | Jansen et al. |
| 2008/0058674 A1* | 3/2008 | Jansen et al. ............. 600/567 |
| 2008/0091215 A1 | 4/2008 | Saleh |
| 2008/0228171 A1 | 9/2008 | Kugler et al. |

* cited by examiner

CUTTING DEVICE AND RELATED METHODS OF USE

CROSS-REFERENCE TO RELATED APPLICATIONS

This application is based upon and claims the benefit of priority under 35 U.S.C. §119(e) of U.S. Provisional Application No. 61/521,844 to Asselin et al. filed on Aug. 10, 2011, the complete disclosure of which is incorporated by reference herein.

FIELD OF THE INVENTION

Embodiments of this invention relate generally to medical devices and procedures. In particular, embodiments of the instant invention relate to medical devices and procedures for assisting in the capture and cutting of tissue or foreign matter from a body portion.

BACKGROUND OF THE INVENTION

Organic material (e.g., blood clots, tissue, and biological concretions such as urinary, biliary, and pancreatic stones) or inorganic material (e.g., components of medical devices or other foreign matter) may sometimes obstruct or otherwise be present within the body's anatomical lumens, such as the biliary tree. For example, biological concretions can develop in certain parts of the body, such as kidneys, pancreas, and gallbladder. Minimally invasive medical procedures generally involve causing limited trauma to the tissues of the patient, and can be used to dispose of certain problematic biological concretions or similarly unwanted obstructions.

Many medical retrieval devices can be used to entrap an object, such as tissue or a stone fragment, and drag it through an ampulla (i.e., a small dilatation in the patient's anatomical lumen) to remove it. Such medical retrieval devices include, for example, retrieval baskets and may be used through an endoscope or laparoscope. However, occasionally an object may be too large to be extracted through an ampulla.

With many known retrieval assemblies, it is difficult to cut the entrapped material, such as tissue or a stone, once the material is entrapped to reduce the size of the material. For example, in some patients, a cicatrix or some other constriction that reduces the diameter of a body lumen may form within the lumen. The narrowed lumen may not interfere or prevent normal insertion of a retrieval device. However, after the retrieval device is inserted into the tract, the retrieval assembly expands, and an object is captured within the device. At this point, the diameter of the retrieval assembly containing the entrapped object may exceed the inner diameter of the narrowed lumen. Under these circumstances, it may be desirable to reduce the size of the entrapped object so that the retrieval assembly and the entrapped object may be safely removed from the lumen. Other circumstances may be encountered during a medical retrieval procedure that may also require cutting an entrapped object within a retrieval device.

The present disclosure provides medical retrieval devices and methods of using the same that address some or all of the aforementioned shortcomings of the existing devices.

SUMMARY OF THE INVENTION

It is an object of the invention to provide a medical instrument, i.e., a medical retrieval device with features that permit retrieval of material within a body. The material can be biological material, such as tissue and stones, or foreign material, or any variety of other types of material within a body. The material can be located in a urinary or biliary tract or elsewhere in the body.

Embodiments of the invention provide a medical device and procedure that assists practitioners in the removal of tissue or foreign matter from a desired body portion by entrapment and cuts the tissue or foreign matter when desired.

In accordance with an aspect of the present disclosure, a medical device may include a sheath having a proximal end and a distal end; a cutting device at the distal end of the sheath; a lumen extending longitudinally through both the sheath and the cutting device; an elongate member extending within the lumen and moveable relative to the sheath and the cutting device; and a retrieval assembly connected to the elongate member and retractable within and extendable from the lumen of the sheath.

Various embodiments of the invention may include one or more of the following aspects: the cutting device may be a hypotube having a sharp distal edge; the cutting device may comprise a first material and the sheath may comprise a second material different from the first material; the distal end of the cutting device may have an edge configured to cut an object entrapped in the retrieval assembly; the edge may be circular and the distal end of the cutting device may include a wall that tapers to the circular edge; an outer diameter of the cutting device may be substantially constant, and an inner diameter of the cutting device may increase toward the edge; the distal end of the cutting device may further comprise a cutting wire; the retrieval assembly may comprise a plurality of legs, and at least one of the plurality of legs may comprise an inward facing sharp edge; and the medical device may comprise an energy generator configured to generate at least one of an RF energy, ultrasonic energy, and heat to a tissue sample positioned in the retrieval assembly.

A further aspect of the present disclosure includes a method of entrapping an object within a body. The method includes inserting a medical device into a body lumen, the medical device having a sheath having a proximal end and a distal end, a cutting device at the distal end of the sheath, a lumen extending longitudinally through both the sheath and the cutting device, an elongate member extending within the lumen and moveable relative to the sheath and cutting device, and a retrieval assembly connected to the elongate member and retractable within and extendable from the lumen of the sheath. The method further includes advancing the medical device to a site within the body lumen, extending the elongate member and retrieval assembly distally relative to the sheath and cutting device to deploy the retrieval assembly, and entrapping the object within the retrieval assembly.

Various embodiments of the invention may include one or more of the following aspects: the method may further comprise the step of generating at least one of RF energy, ultrasonic energy, and heat to cut a portion of the object, the step of retracting the elongate member and retrieval assembly proximally relative to the sheath and cutting device after the step of entrapping the object within the retrieval assembly to cut a portion of the object; the step of rotating the elongate member and retrieval assembly relative to the cutting device during the step of retracting the portion of the object; the distal end of the cutting device may have an edge configured to cut the portion of the object during the retracting step; the edge may be circular and the distal end of the cutting device may include a wall that tapers to the circular edge; an outer diameter of the cutting device may be substantially constant, and an inner diameter of the cutting device may increase toward the edge; and the retrieval assembly may comprise a plurality of legs, and the plurality of legs may comprise an inward facing sharp edge.

A further aspect of the present disclosure includes a method of cutting tissue from a tissue sample. The method includes inserting a medical device into a body lumen, the medical device having a device lumen having a distal end, a cutting device disposed at the distal end of the device lumen, an elongate member extending within and axially displaceable with respect to the device lumen, and a retrieval member disposed on a distal end of the elongate member. The method further includes advancing the medical device to a site within the body lumen, entrapping the tissue sample within the retrieval assembly, and axially displacing the elongate member and retrieval assembly relative to the cutting device to cut tissue from the tissue sample.

Various embodiments of the invention may include one or more of the following aspects: the distal end of the cutting device may further comprise a cutting wire; the distal end of the cutting device may have an edge configured to cut an object entrapped in the retrieval member; the edge may be circular and the distal end of the cutting device may include a wall that tapers to the circular edge; and the retrieval member may comprise a plurality of legs, and the plurality of legs may comprise an inward facing sharp edge.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which is are illustrated in the accompanying drawings. Wherever possible, the same reference numbers will be used throughout the drawings to refer to the same or like parts. As used in this disclosure, "distal" refers to a position or direction furthest from a user of the device and "proximal" refers to a position or direction opposite "distal" and closest to the user.

FIGS. 1-4 depict certain configurations of an exemplary embodiment of a medical device 10. The medical device 10 includes a sheath 11, an elongate member 12, a cutting device 13, and a retrieval assembly 14.

Figure 1:
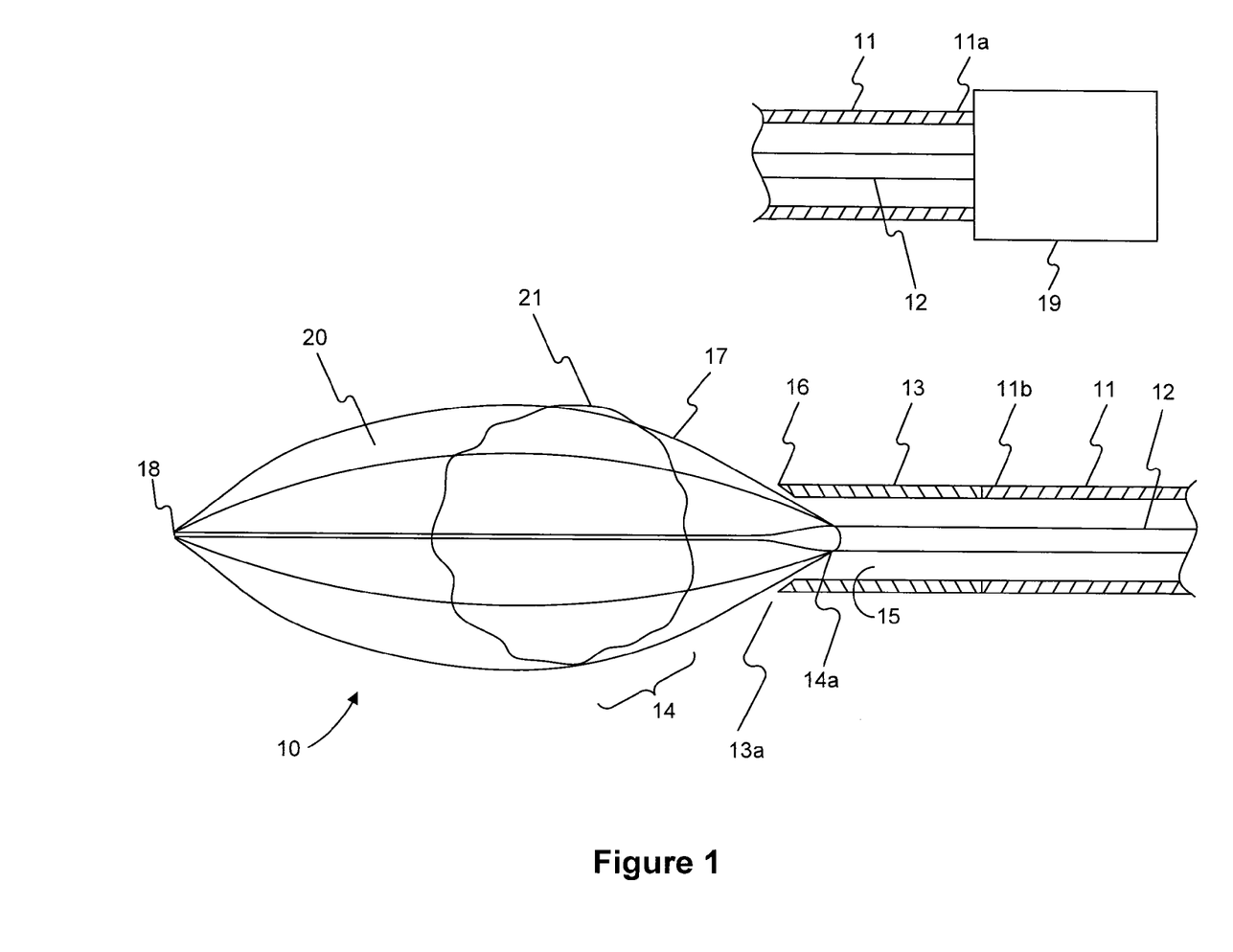
FIG. 1 is a schematic representation of a medical device in an expanded and extended position according to an embodiment of the present invention.

Sheath 11 includes a proximal end 11a and a distal end 11b, and may be any suitable sheath or catheter known in the art. Sheath 11 may be fabricated by any known process such as, for example, extrusion. In addition, sheath 11 may be made from any suitable material that provides sufficient strength and flexibility for adequate operation, but which is soft enough to avoid trauma or irritation to a body lumen in which sheath 11 may be deployed. Such material may include, but is not limited to, polyurethane and/or silicone. Sheath 11 may have any desired cross-sectional shape and/or configuration. For example, sheath 11 may also have one or more cross-sectional shapes and/or configurations along its length, and may be any desired dimension suitable for deployment within a desired body lumen. For example, sheath 11 may have dimensions adapted for placement in a biliary duct having a particular size. For instance, sheath 11 may have an outer periphery that is substantially the same size as, or a size less than, the inner periphery of a biliary duct. The overall length and diameter of sheath 11 may vary depending on the application. For example, a relatively long sheath 11 may be advantageous for retrieving stones or other concretions deep within the body of a patient. Sheath 11 may also be flexible along at least a portion of its length so that it may bend as it is advanced through tortuous body lumens.

Sheath 11 may further include at least one lumen 15 extending therethrough. In some embodiments, lumen 15 may be defined as an internal passageway with an entrance and an exit, and may be formed by any suitable process such as, for example, extrusion. Alternatively, sheath 11 may include a plurality of lumens (not shown) that may or may not differ in size. In such embodiments, the plurality of lumens may provide passageways useful in delivering, or removing, for example, medical devices, fluids, and/or structures to or from a treatment site. Lumen 15 provided within sheath 11 may have any cross-sectional shape, dimension, and/or configuration. For example, in some embodiments, lumen 15 may have a substantially circular cross-section.

Cutting device 13 may be located at distal end 11b of sheath 11. In some embodiments, cutting device 13 may be fabricated independently from sheath 11 as depicted in FIG. 1. For example, cutting device 13 may be a hypotube blade. In addition, cutting device 13 may be configured to retract into and extend from sheath 11. Alternatively, in another embodiment, cutting device 13 may be formed integral with sheath 11. Cutting device 13 may be formed by any suitable process such as, for example, extrusion. In addition, cutting device 13 may be made from any suitable material that provides sufficient strength to cut a material within a body, such as tissue and stones, or foreign material, or any variety of other types of material within a body. Such material may include, but is not limited to, nylon, urethane, polyamide, PEBAX, stainless steel (such as 300 and 400 series including 316L, 304, 445), cobalt, chromium, nickel, titanium, nitinol, thermoforming plastic, polytetrafluoroethylene ("PTFE"), and expanded polytetrafluoroethylene ("ePTFE"). Cutting device 13 may be formed of a material that is stiffer than the material forming sheath 11. Lumen 15 also extends through cutting device 13.

Figure 4:
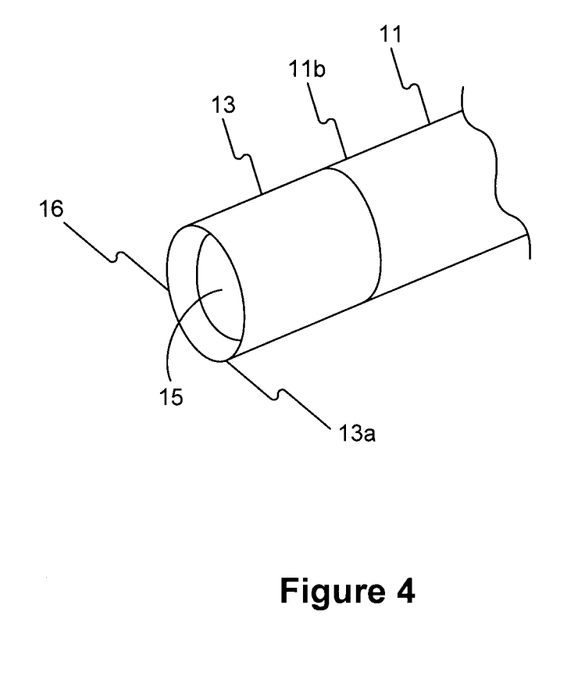
FIG. 4 is an isometric representation of a cutting device portion of the device in FIG. 1

Cutting device 13 may have a distal end 13a with an edge 16. Distal end 13a of cutting device 13 may taper at edge 16. Distal end 13a of cutting device 13 may have an inner diameter that increases toward edge 16. For example, cutting device 13 may have a constant outer diameter and an inner diameter that increases toward edge 16 such that edge 16 is sharp.

Figure 7:
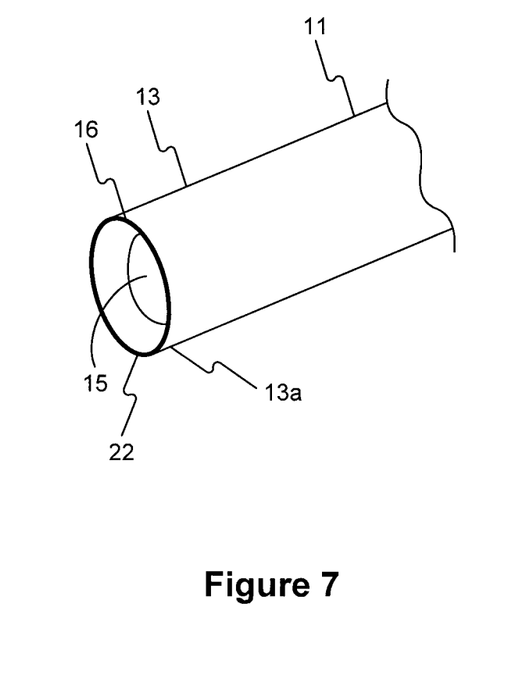
FIG. 7 is an isometric representation of a cutting device portion of a medical device according to an embodiment of the present invention.

Alternatively, or in addition to, cutting device 13 tapering toward edge 16, cutting device 13 may include a cutting wire 22 at proximal end 13a, as shown in FIG. 7. The cutting wire 22 may be sufficiently thin and therefore sharp that the cutting wire 22 cuts tissue when brought into contact with and/or moved relative to the desired tissue. The cutting wire 22 may be electrically active (having either a monopolar or bipolar configuration) so as to assist in cutting tissue. If conductive, the cutting wire 22 may be electrically connected to a suitable power source known in the art (e.g., RF generator) via suitable electrical connections known in the art (e.g., electrical leads and/or wires). The power source may be disposed anywhere on or relative to the medical device 10, for example, at or connected to a handle 19.

Elongate member 12 is longitudinally disposed and slideably moveable in lumen 15 of sheath 11 and cutting device 13. Elongate member 12 may be formed from, for example, a rod, tube, cannula, wire, stent, or other like structure. Alternatively, the elongate member 12 may also be formed from a portion of a cylindrical piece of material, or from a flat sheet of material. If formed from a flat sheet, elongate member 12 may be formed into a cylindrical shape to facilitate the fabrication of retrieval assembly 14.

Elongate member 12 may be formed from any biocompatible material known in the art. Such materials may include, but are not limited to, stainless steel, cobalt chromium, nickel, titanium, nitinol, thermoforming plastics, PTFE, and EPTFE. In addition, elongate member 12 may also be a metal with one or more coatings such as, for example, a polymer.

Elongate member 12 may have any desired cross-sectional shape and/or configuration. For example, elongate member 12 may have a substantially circular cross-section. In addition, elongate member 12 may have one or more cross-sectional shapes and/or configurations along its length, and may have any desired dimension suitable for deployment in a desired body lumen, and retraction into sheath 11 and cutting device 13. For example, elongate member 12 may have an outer periphery that facilitates insertion into sheath 11, and permits longitudinal movement of elongate member 12 relative to sheath 11. The overall length and diameter of elongate member 12 may vary depending on the application. For example, a relatively long elongate member 12 may be advantageous for retrieving tissue, stones, or other unwanted objects deep within the body of a patient. In addition, elongate member 12, having a relatively small diameter, may be advantageous for retrieving unwanted objects from restricted passageways within the human urinary tract.

Elongate member 12 may include a number of any desired flexibility features (not shown) to increase maneuverability of the device 10 while the device 10 is within the body of a patient. The flexibility features, for example, may be cut into a distal portion of elongate member 12. However, flexibility features may be positioned anywhere along the length of the elongate member 12, and may be created by any suitable process known in the art.

In some embodiments, elongate member 12 may further include one or more internal lumens (not shown) extending therethrough. In such embodiments, the lumens may provide passageways useful in delivering, or removing, for example, medical devices such as laser fibers, fluids, and/or other structures to or from a treatment site.

Retrieval assembly 14 extends distally from a distal end of elongate member 12, and may be, for example, a basket having any desired number of legs 17. In addition, retrieval assembly 14 may be retractable within and extendable from lumen 15 of sheath 11 and cutting device 13. The retrieval assembly 14 may be manufactured from any suitable biocompatible material, for example, one or more metals and/or composites, such as, but not limited to, 400 series stainless steel, Ti-Beta-3 titanium alloys, cobalt chromium alloys, and nitinol. Retrieval assembly 14 may have desired cross-sectional shape and/or configuration. For example, retrieval assembly 14 may also have one or more cross-sectional shapes and/or configurations along its length, and any desired dimensions suitable for deployment in a desired body lumen. For example, retrieval assembly 14 may have dimensions adapted for placement in a biliary duct having a particular size. For instance, retrieval assembly 14, in an expanded state, may have an outer periphery that is substantially the same size as, or less than, the inner periphery of a biliary duct. In addition, retrieval assembly 14 may have configurations, dimensions, and/or material properties that permit longitudinal movement of retrieval assembly 14 relative to sheath 11 and cutting device 13 and extension and retraction into and out of sheath 11 and cutting device 13. The overall length and diameter of retrieval assembly 14 may vary depending on the application. For example, a relatively small diameter may be advantageous for retrieving tissue, stones, or other unwanted objects from restricted passageways within the human urinary tract. Retrieval assembly 14 may also be collapsible so that it may be more easily advanced through body lumens in its collapsed state, and when desired expandable for deployment. For example, retrieval assembly 14 may be made from certain materials and according to certain methods so that retrieval assembly 14 may self-expand when extended from lumen 15 of sheath 11 and cutting device 13, as is known in the art. Alternatively, retrieval assembly 14 may be expanded in any other suitable manner known in the art.

Retrieval assembly 14 may be made out of the same piece of material as elongate member 12. Alternatively, retrieval assembly 14 may be fabricated independently by any known means, and may then be made integral with elongate member 12 through connection of a proximal end 14a of retrieval assembly 14 to a region of elongate member 12, such as the distal end of elongate member 12. Connection of proximal end 14a of retrieval assembly 14 to elongate member 12 may be accomplished through any suitable means of fixedly connecting retrieval assembly 14 to elongate member 12. For example, possible connections may include, but are not limited to, welding, soldering, and/or crimping.

Legs 17 of retrieval assembly 14 may be formed by, for example, laser cutting, chemical etching, die cutting, or mechanically slicing a single piece of material. As a result, the width of the cuts may define the width and mechanical behavior of each of legs 17, and the desired width of the cuts may vary depending on the particular application. For example, it may be advantageous to have relatively narrow basket legs when retrieving a relatively large unwanted object from within the body. In certain instances, legs 17 may be formed by, for example, welding, soldering, tying, or otherwise connecting separate pieces of wire or other material together. In such instances, legs 17 may or may not be made with the same materials.

Although FIG. 1 shows that retrieval assembly 14 comprises six legs, retrieval assembly 14 may include any number of legs to facilitate retrieval of unwanted objects from within a patient's body. Legs 17 may have any desired pattern, configuration, and characteristic suitable for entrapping objects within an anatomical lumen. For example, legs 17 may be cylindrical, flat, square, semi-circular, rectangular, or any other suitable shape suitable for entrapping objects from within a patient's body. In addition, legs 17 may be any cross-sectional shape known in the art including, but not limited to, circular, flat, square, or ovular. Additionally, legs 17 may be made of a material exhibiting shape memory, as is known in the art.

In some embodiments, at least a portion of at least one of the legs 17 may include an inward facing surface textured to improve the retrieval capabilities of device 10. For example, possible structures that may be used as texture may include, but are not limited to, indentations, teeth, spikes, treads, and serrations. The texture of the inward facing surface may provide multi-point contact with objects targeted for entrapment and may be pointed away from the sensitive tissue within the body structure so as not to cause trauma thereto. Furthermore, at least a point of at least one of the legs 17 may be coated with, for example, a layer of PTFE, EPTFE, polyvinylethylene, or any other material suitable for protecting legs 17 during processes such as, for example, laser lithotripsy.

Retrieval assembly 14 may include a plurality of cells or spaces 20 between legs 17. Spaces 20 may be of any suitable shape, size, and/or configuration, and may be configured to accommodate and allow objects to pass into the interior of the retrieval assembly 14 for entrapment and, if desired, subsequent removal from the body. Furthermore, the size of spaces 20 between legs 17 may vary or be consistent.

The distal end of each of legs 17 may connect at tip 18 as depicted in FIG. 1. Tip 18 may further be sized and shaped to assist in the capture and retrieval of unwanted objects within a patient's body. For example, tip 18 may be blunt, rounded, flat, smooth, knotted, or any other atraumatic shape known in the art, and may or may not be composed of the same material as legs 17. Tip 18 may be as small as possible so as not to interfere with the capture and retrieval of the targeted object. Furthermore, tip 18 may be formed by soldering, welding, cementing, tying, or otherwise connecting the distal ends of legs 18 together, and may or may not contain fillers such as, for example, epoxy. Alternatively, the distal end of each of legs 17 may be free.

Figure 2:
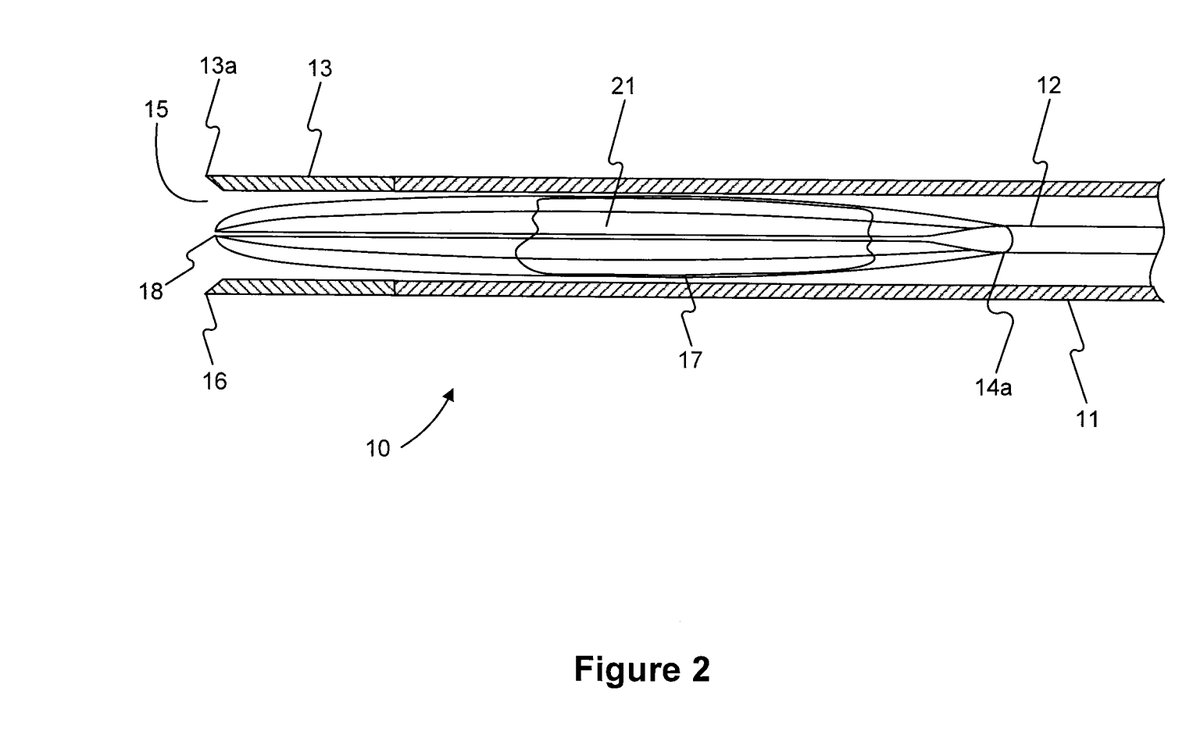
FIG. 2 is a schematic representation of the device in FIG. 1 in a retracted and collapsed position.
Figure 3:
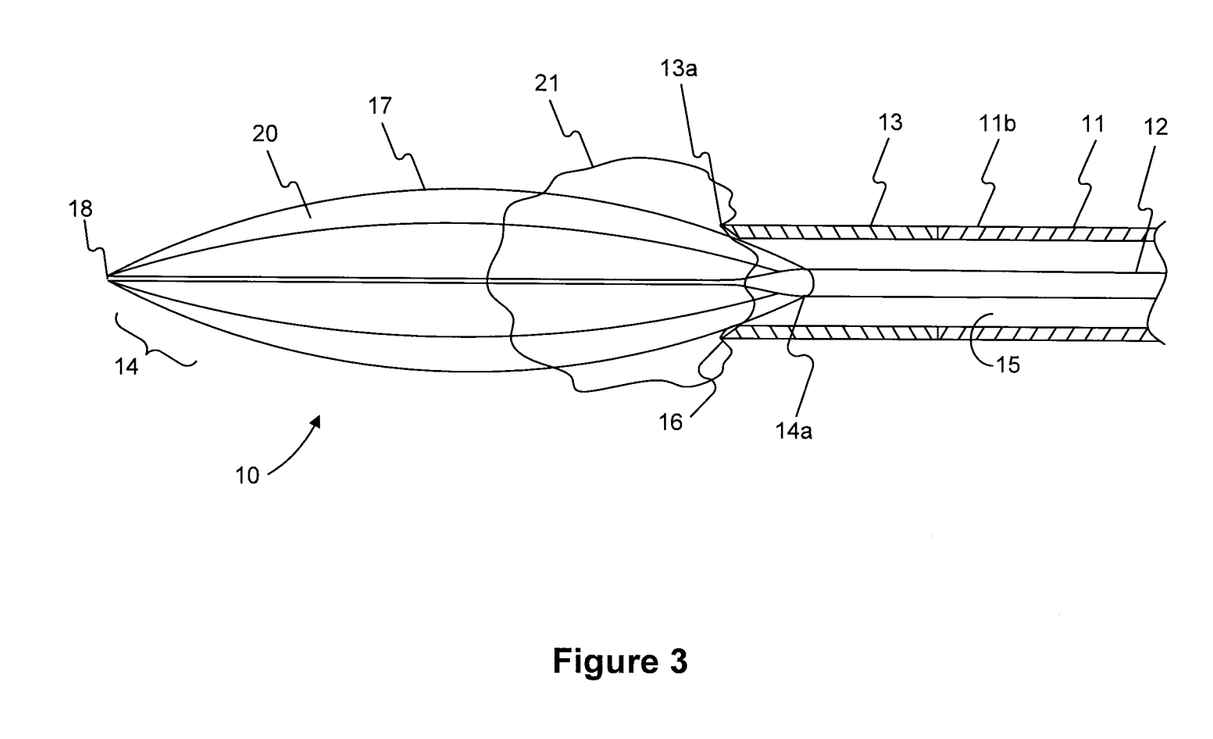
FIG. 3 is a schematic representation of the device in FIG. 1 in a partially retracted state.

Retrieval assembly 14, depicted and described in FIGS. 1-3, is an exemplary retrieval assembly that may be used in the method and device of the present invention. Any other suitable retrieval assembly capable of entrapping, releasing, and/or removing objects from within a body lumen may be used.

Figure 5:
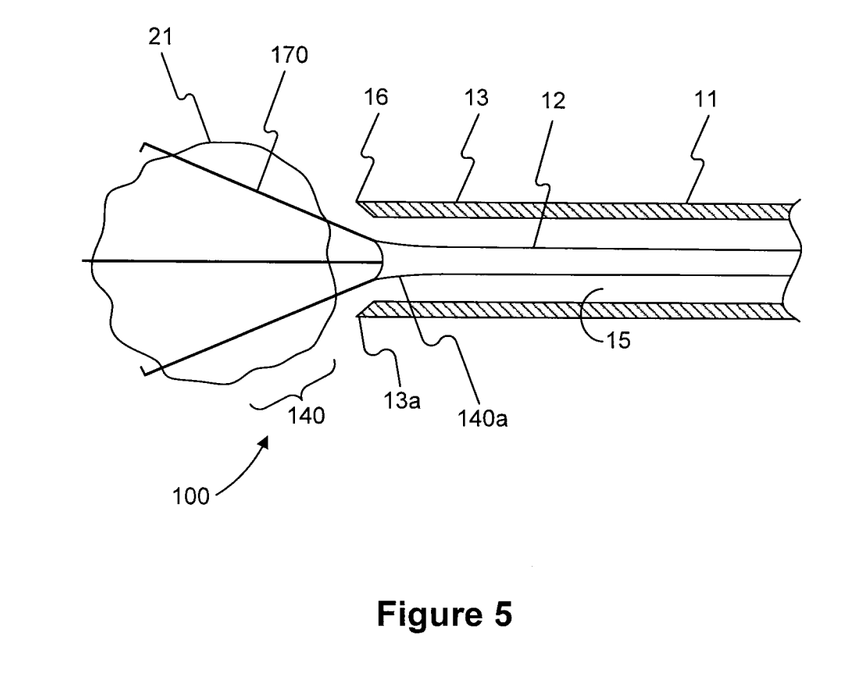
FIG. 5 is a schematic representation of a medical device in an expanded and extended position according to an embodiment of the present invention.
Figure 6:
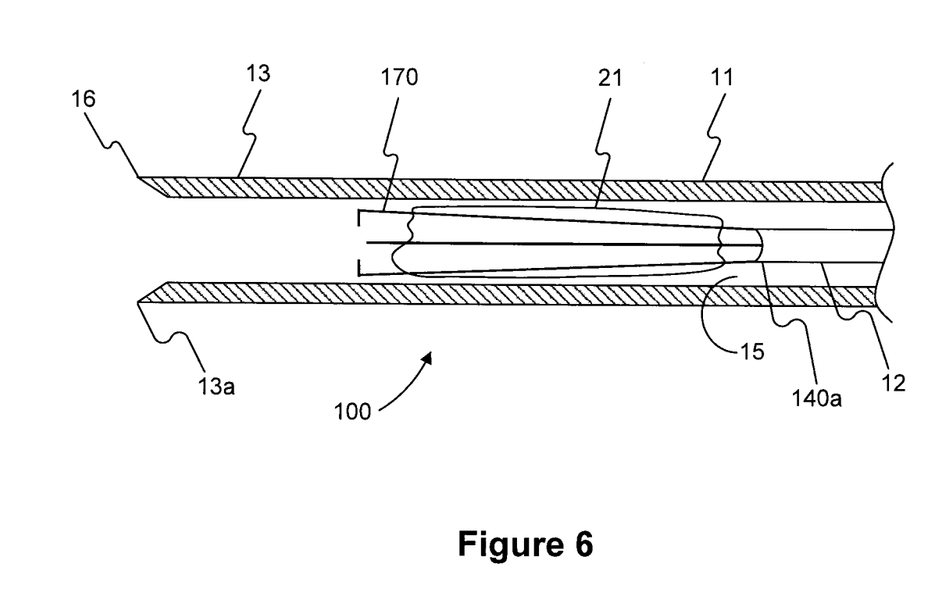
FIG. 6 is a schematic representation of the device in FIG. 5 in a retracted and collapsed position.

Retrieval assembly 140, depicted and described in FIGS. 5 and 6, is a further exemplary retrieval assembly that may be used in the method and device of the present invention. Retrieval assembly 140 may include the features discussed above with respect to retrieval assembly 14 unless otherwise noted. For example, retrieval assembly 140 may be manufactured by similar processes and materials as retrieval assembly 14.

Retrieval assembly 140 extends distally from a distal end of elongate member 12, and may be, for example, a grasper. Although FIG. 5 shows that retrieval assembly 140 comprises four legs, retrieval assembly 140 may include any number of legs to facilitate retrieval of unwanted objects from within a patient's body. In some embodiments, at least a portion of at least one of the legs 170 may include an inward facing surface textured to improve the retrieval capabilities of device 100. For example, legs 170 may include inwardly facing barbs on a distal end of each of legs 170. Furthermore, possible structures that may be used as texture may include, but are not limited to, indentations, teeth, spikes, treads, and serrations.

As depicted in FIGS. 1, 2, 5, and 6, retrieval assembly 14, 140 may be configured to collapse and expand as desired. For example, retrieval assembly 14, 140 may be configured to be collapsible such that it facilitates retraction into lumen 15 of sheath 11 as depicted in FIGS. 2 and 6, and/or advanced out of sheath 11, such that retrieval assembly 14, 140 at least partially expands and/or fully expands as depicted in FIGS. 1 and 5. In such an example, retrieval assembly 14, 140 may be collapsed and retracted into lumen 15 of sheath 11 and cutting device 13, while sheath 11 and cutting device 13 are being advanced through a body lumen to a desired body location. Once sheath 11 is positioned in the desired body location, retrieval assembly 14, 140 may be advanced out of sheath 11 and cutting device 13 for expansion.

Retrieval assembly 14, 140 may be retracted into and/or advanced out of lumen 15 using any method known in the art. For example, by means of the connection between proximal end 1a, 140a and elongate member 12, movement of elongate member 12 relative to sheath 11 and cutting device 13 causes retrieval assembly 14, 140 to also move relative to sheath 11 and cutting device 13 allowing retrieval assembly 14, 140 to be retracted into and/or advanced out of sheath 11 and cutting device 13. Any suitable known handle 19 may be used at the proximal user end of sheath 11 and/or elongate member 12 for actuation.

Figures 8A, 8B, 8C:
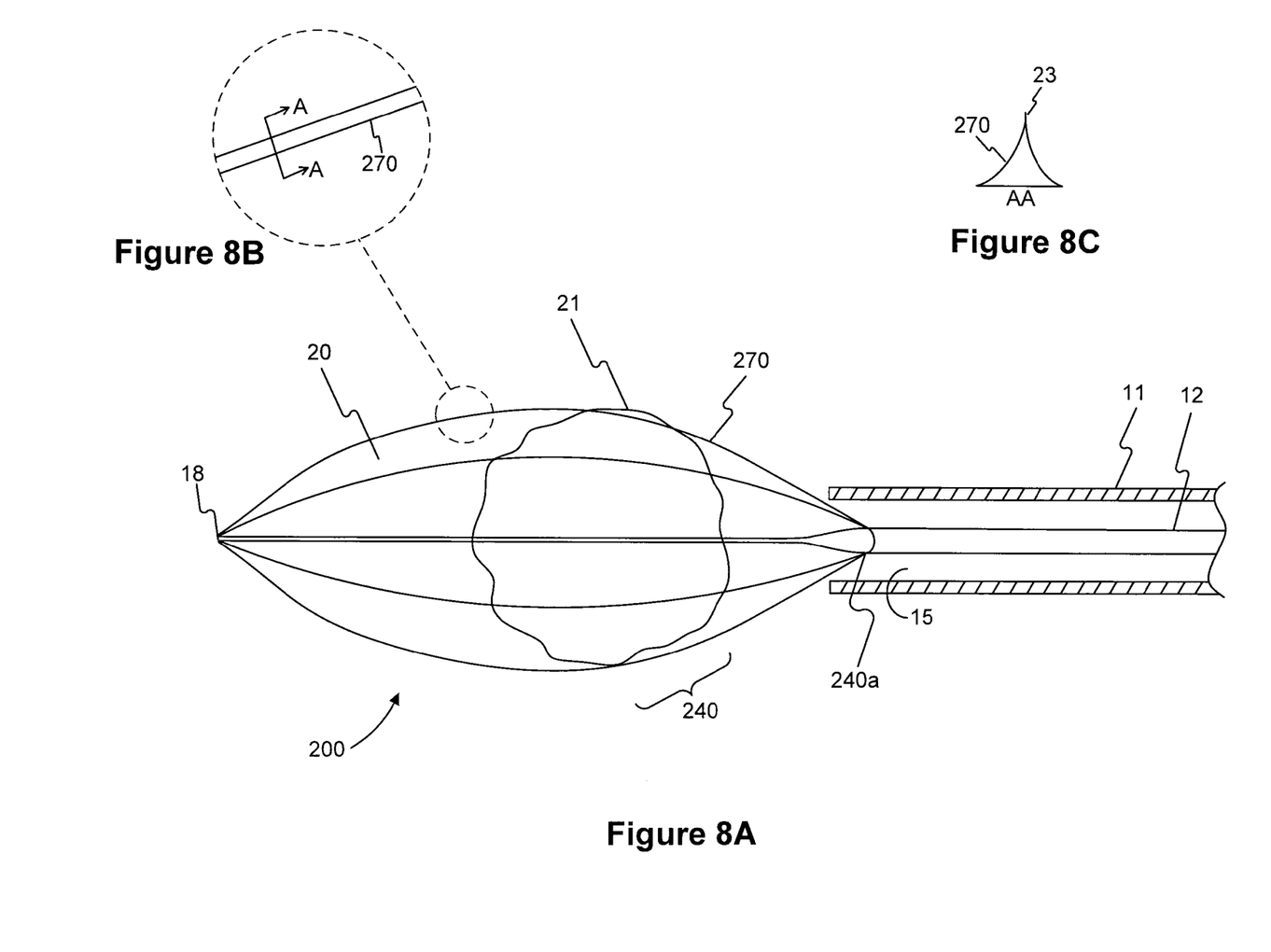
FIG. 8A is a schematic representation of a medical device in an expanded and extended position according to an embodiment of the present invention.
FIG. 8B is an expanded view of a portion of a leg of the medical device in FIG. 8A.
FIG. 8C is a cross-sectional view of the leg in FIG. 8B.

Retrieval assembly 240, depicted and described in FIGS. 8A-8C, is a further exemplary retrieval assembly that may be used in the method and device of the present invention. Retrieval assembly 240 may include the features discussed above with respect to retrieval assembly 14, 140 unless otherwise noted. For example, retrieval assembly 240 may be manufactured by similar processes and materials as retrieval assembly 14, 140.

Retrieval assembly 240 extends distally from a distal end of elongate member 12, and may be, for example, a basket. Although FIG. 8A shows that retrieval assembly 240 comprises six legs, retrieval assembly 240 may include any number of legs to facilitate retrieval of unwanted objects from within a patient's body. In some embodiments, at least one of legs 270 may include an inward facing sharp cutting edge 23 as depicted in FIG. 8C. In an embodiment, each of legs 270 includes a sharp edge 23. A cross-section of leg 270 may be a triangular or a three-sided shape with two curved, concave sides forming the sharp cutting edge 23.

In some embodiments, retrieval assembly 240 may be used in conjunction with sheath 11 and cutting device 13. In alternative embodiments, retrieval device 240 may be used in conjunction with sheath 11 and without cutting device 13.

Figure 9:
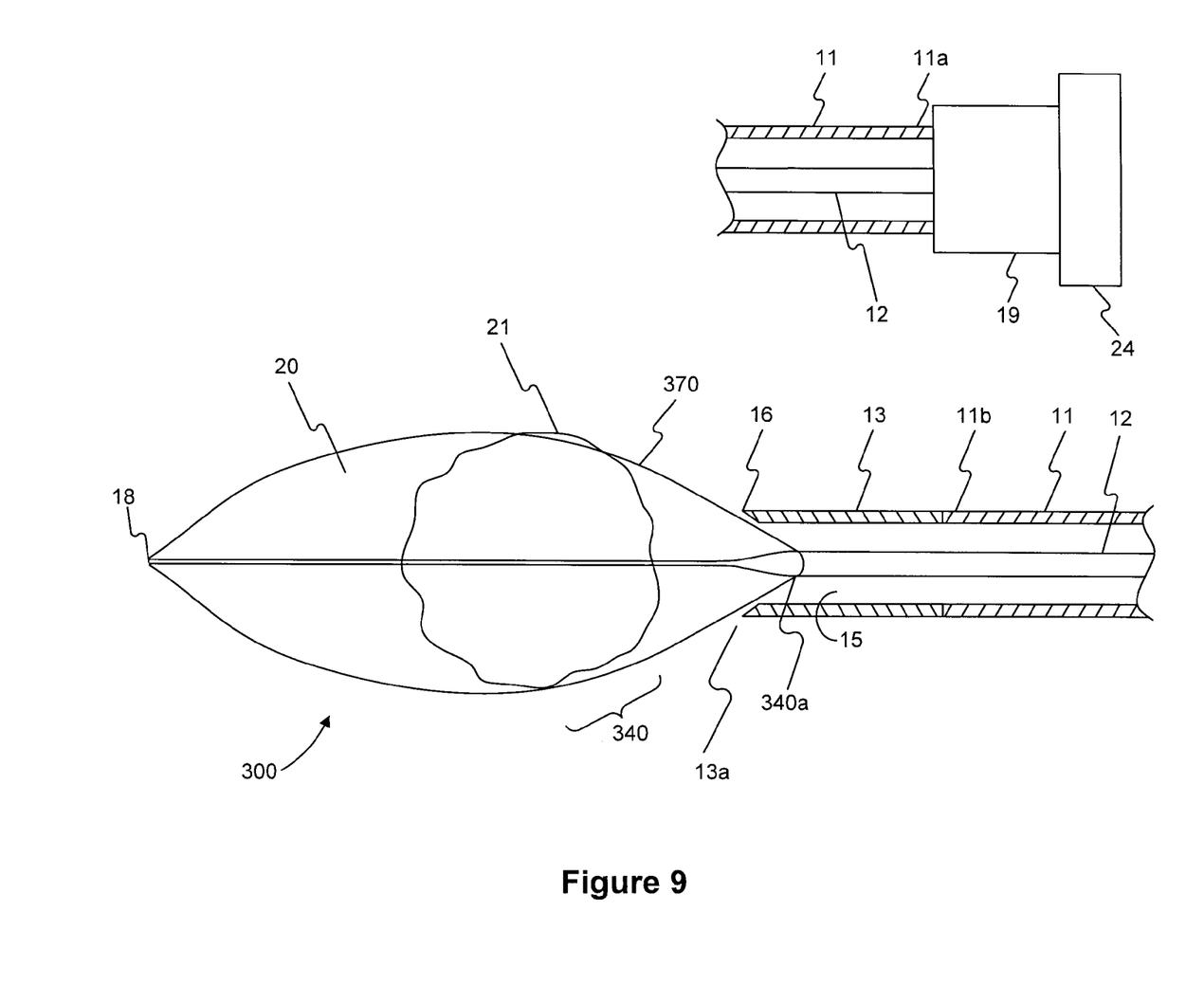
FIG. 9 is a schematic representation of a medical device in an expanded and extended position according to an embodiment of the present invention.

Retrieval assembly 340, depicted and described in FIG. 9, is a further exemplary retrieval assembly that may be used in the method and device of the present invention. Retrieval assembly 340 may include the features discussed above with respect to retrieval assembly 14, 140, 240 unless otherwise noted. For example, retrieval assembly 340 may be manufactured by similar processes and materials as retrieval assembly 14, 140, 240.

Retrieval assembly 340 extends distally from a distal end of elongate member 12, and may be, for example, a basket. Although FIG. 9 shows that retrieval assembly 340 comprises three legs, retrieval assembly 340 may include any number of legs to facilitate retrieval of unwanted objects from within a patient's body. In some embodiments, retrieval assembly 340 may be connected to a radio frequency generator 24. Generator 24 may be integral with handle 19, or generator 24 may be a separate structure that is coupled to handle 19 through any suitable connection. Generator 24 is electrically connected to elongate member 12 and legs 370 through any suitable electrical connection. In some embodiments, legs 370 may be formed from nitinol. Alternatively, legs 370 may be formed of the same materials as legs 17. Furthermore, retrieval assembly 340 may be greater than 24 French size when in the expanded configuration, and sheath 12 may be 8 French size. Alternatively, retrieval assembly 340 and sheath 12 may be alternative sizes.

In some embodiments, retrieval assembly 340 may be used in conjunction with sheath 11 and cutting device 13. In alternative embodiments, retrieval device 340 may be used in conjunction with sheath 11 and without cutting device 13.

Figure 10:
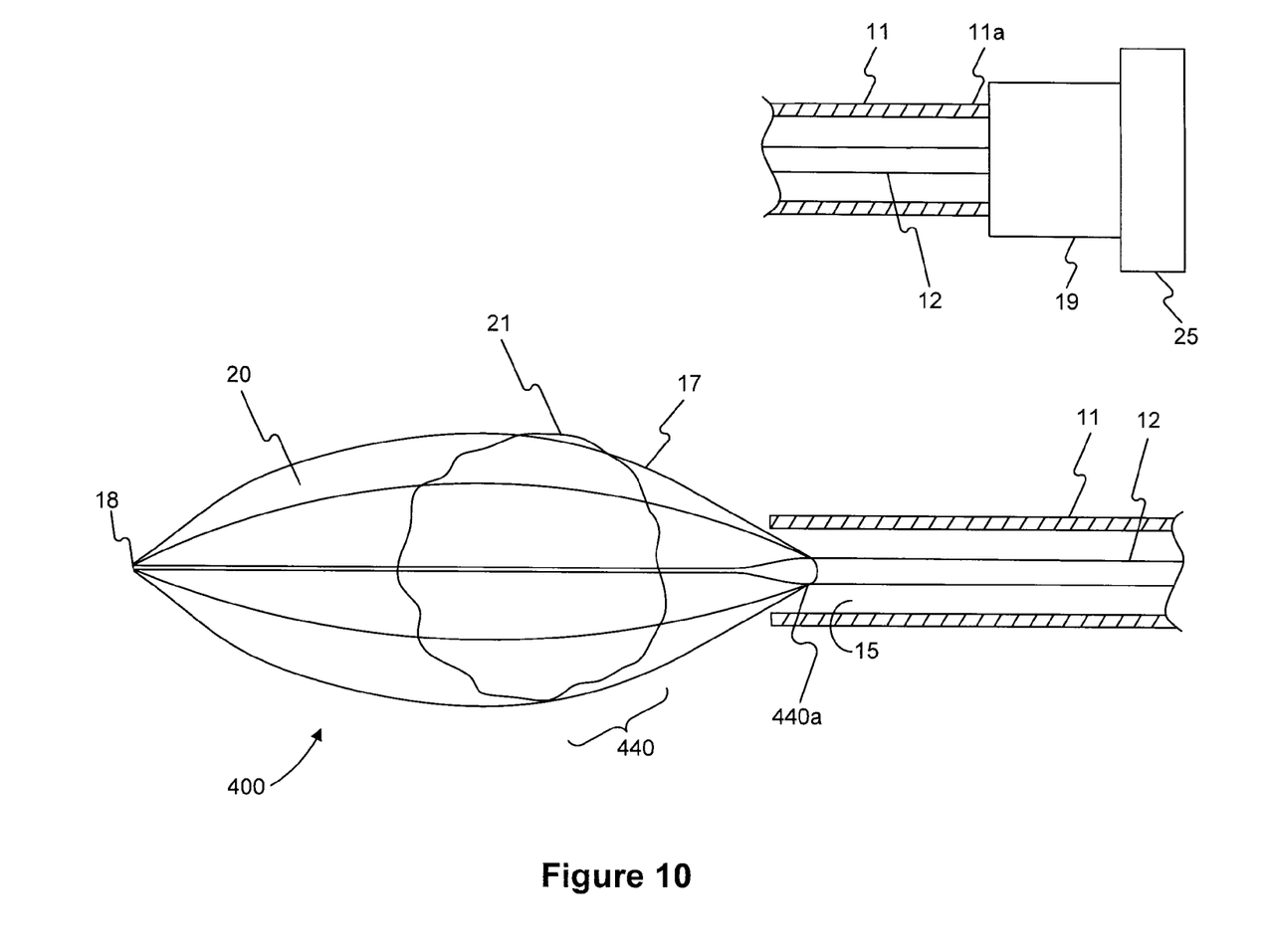
FIG. 10 is a schematic representation of a medical device in an expanded and extended position according to an embodiment of the present invention.

Retrieval assembly 440, depicted and described in FIG. 10, is a further exemplary retrieval assembly that may be used in the method and device of the present invention. Retrieval assembly 440 may include the features discussed above with respect to retrieval assembly 14, 140, 240, 340 unless otherwise noted. For example, retrieval assembly 440 may be manufactured by similar processes and materials as retrieval assembly 14, 140, 240, 340.

Retrieval assembly 440 extends distally from a distal end of elongate member 12, and may be, for example, a basket. Although FIG. 10 shows that retrieval assembly 440 comprises six legs, retrieval assembly 440 may include any number of legs to facilitate retrieval of unwanted objects from within a patient's body. In some embodiments, retrieval assembly 440 may be connected to an emitter 25 which emits for example either ultrasonic energy or heat. Emitter 25 may be integral with handle 19, or emitter 25 may be a separate structure that is coupled to handle 19 through any suitable connection. Emitter 25 is electrically connected to elongate member 12 and legs 17 through any suitable electrical connection.

In some embodiments, retrieval assembly 440 may be used in conjunction with sheath 11 and cutting device 13. In alternative embodiments, retrieval device 240 may be used in conjunction with sheath 11 and without cutting device 13.

In reference to FIGS. 1-10, embodiments of the invention may include methods of using the medical device 10, 100, 200, 300, 400 of the present disclosure to retrieve tissue, stones, and other unwanted materials located in the bladder, ureter, kidney, or other body structures. Medical device 10, 100, 200, 300, 400 may be used in an environment that is relatively fluid filled or that is relatively dry. The medical device 10, 100, 200, 300, 400 may be inserted through the urethra of a patient or, alternatively, the medical device may be inserted percutaneously. The medical device 10, 100, 200, 300, 400 may be used in any location of the body in which a passageway or orifice includes unwanted material to be removed and/or is being at least partially blocked.

The medical device 10, 100, 200, 300, 400 may be advanced to a treatment site in a number of different ways. For example, the device 10, 100, 200, 300, 400 may be advanced to a desired body location over a guide wire (not shown), wherein the desired body location may correspond to the vicinity of a tissue, stone, or another object targeted for removal. The medical device 10, 100, 200, 300, 400 may also be advanced to the treatment site through an access sheath or any other access device known in the art.

Alternatively, the medical device 10, 100, 200, 300, 400 may be fed to the desired body location by means of an imaging device, and may travel through the body without the use of a guide wire or access sheath. To facilitate such feeding, sheath 11 may include radiopaque bands (not shown) detectable by x-ray or other imaging means. Thus, the user may monitor the position of the medical device 10, 100, 200, 300, 400 and movement thereof through the use of an imaging device.

As yet another alternative, the medical device 10, 100, 200, 300, 400 may be used in conjunction with an endoscope (not shown) or any other type of intracorporeal scope known in the art. The endoscope may travel through the body to the treatment site in any conventional manner. Once the endoscope is positioned adjacent to the treatment site, the medical device 10, 100, 200, 300, 400 may be fed through an access port of the endoscopic sheath to gain access to the object targeted for retrieval, such as tissue.

The object targeted for retrieval may be, for example, tissue sample 21. The object targeted for retrieval may include any unwanted object commonly removed from a body structure or passageway. The objects may be of any size and/or shape. Furthermore, the medical device 10, 100, 200, 300, 400 may be used to remove objects that are both impacted and free floating.

In clinical applications where an endoscope (not shown) or other similar access device is used for access, the endoscope may be advanced through a tortuous body lumen and to a desired body location. With retrieval assembly 14, 140, 240, 340, 440 disposed inside of sheath 11 and in a collapsed and retracted state, the medical device 10, 100, 200, 300, 400 may then be inserted into the body lumen by feeding the medical device 10, 100, 200, 300, 400 through an access port in the endoscopic sheath to the desired body location. For example, the medical device 10, 100, 200, 300, 400 may be advanced until the distal end 13*a* of cutting device 13 or the distal end of sheath 11 has reached a desired location, such as, a short distance past an object targeted for entrapment and/or removal. The method is not limited to the use with any particular object, and may also be used with one or more intracorporeal and/or extracorporeal objects at various locations and of various geometries and compositions.

Once the distal end 13*a* of cutting device 13 or the distal end 11 is advanced past a targeted object, the elongate member 12 may then be advanced distally out of sheath 11 and/or cutting device 13, so that retrieval assembly 14, 140, 240, 340, 440 may deploy and self-expand. For example, this may be achieved by pulling sheath 11 proximally relative to elongate member 12. Any suitable known handle assemblies may be used to effect deployment and expansion of retrieval assembly 14, 140, 240, 340, 440. When fully deployed, retrieval assembly 14, 140, 240, 340, 440 may be substantially cylindrically shaped or have any other configuration suitable to the particular size and shape of both the targeted object and/or the environment it is located in. The proximal end 14*a*, 140*a*, 240*a*, 340*a*, 440*a* of retrieval assembly 14, 140, 240, 340, 440 may remain in a collapsed state and/or disposed within the sheath 11, and may be the narrowest portion of retrieval assembly 14, 140, 240, 340, 440.

Once elongate member 12 has been sufficiently advanced out of sheath 11 to allow at least partial deployment and/or expansion of retrieval assembly 14, 140, 240, 340, 440, the medical device may be moved proximally, and sometimes repeatedly, such that the object targeted for entrapment enters the retrieval assembly 14, 140, 240, 340, 440.

The medical device, along with the entrapped object, may then be moved to any desired location, or may be allowed to remain stationary. For example, medical device 10, 100, 200, 300, 400 may be used as an extraction device and removed from the body, assist in immobilizing objects and used as a backstop, or moved to a location more conducive to any additional procedures, such as lithotripsy, surgery, or any other process known in the art.

In certain circumstances, it may be desired to cut the entrapped object to reduce the entrapped object's size before removing the object from the body. To do so, elongate member 12 and retrieval assembly 14, 140, 240, 340, 440 may be retracted into sheath 11 and cutting device 13 while the entrapped object is held in the retrieval assembly 14, 140, 240, 340, 440. For example, this may be accomplished by pulling elongate member 12 proximally relative to sheath 11 so that retrieval assembly 14, 140, 240, 340, 440 begins to retract and collapse into cutting device 13, and consequently, a portion of the entrapped object extending outside of legs 17, 170, 270, 370 in a radial direction is cut away from the remaining portion of the entrapped object inside of legs 17, 170, 270, 370 as depicted in FIG. 3. To assist in cutting away the portion of the entrapped object extending outside of legs 17, 170, 270, 370, elongate member 12 may be rotated relative to sheath 11 and cutting device 13 while being pulled in the proximal direction. Subsequently, the entrapped objected may be pulled completely into lumen 15.

Alternatively, or in addition to, the above-described method for cutting the entrapped object to reduce the entrapped object's size before removing the object from the body, several other methods of reducing the entrapped object's size before removing the object from the body are available. First, for example, elongate member 12 and retrieval assembly 240 may be retracted into sheath 11 while the entrapped object is held in the retrieval assembly 240. For example, this may be accomplished by pulling elongate member 12 proximally relative to sheath 11 so that retrieval assembly 240 begins to retract and collapse into sheath 11, and consequently, a portion of the entrapped object is cut into multiple pieces by the inward facing sharp cutting edges 23 of legs 270. Subsequently, the multiple pieces of the entrapped objected may be pulled completely into lumen 15 or passed naturally though the patient's anatomy.

Second, for example, retrieval assembly 340 may be connected to the radio frequency generator 24. The radio frequency generator 24 may be activated to send RF energy to the retrieval assembly 340. Elongate member 12 and retrieval assembly 340 may then be retracted into sheath 11 while the entrapped object is held in the retrieval assembly 340 such that legs 317 cut the entrapped object into multiple pieces. For example, legs 317 of the retrieval assembly 340 depicted in FIG. 9 would cut the entrapped object into three wedge-shaped pieces. Subsequently, the multiple pieces of the entrapped objected may individually be pulled completely into lumen 15 or passed naturally through the patient's anatomy. Also, prior to activating the radio frequency generator 24, the user may take a sample of the entrapped object by retracting elongate member 12 and retrieval assembly 340 into sheath 11 and cutting device 13 while the entrapped object is held in the retrieval assembly 340 such that a portion of the entrapped object is cut by cutting device 13 and a sample of the cut entrapped object is held in sheath 11 for subsequent testing. The cut portion is, for example, a core of the entrapped object. Alternatively, the cut portion may be a sliver from an edge of the entrapped object.

Third, for example, retrieval assembly 440 may be connected to the emitter 25 which emits for example either ultrasonic energy or heat. The emitter 25 may be activated to send ultrasonic energy or heat to the retrieval assembly 440 and break down the entrapped object into smaller pieces. Subsequently, the multiple pieces of the entrapped objected may be pulled completely into lumen 15 or passed naturally through the patient's anatomy.

By way of example, one advantage of using retrieval assembly 14, 140, 240, 340, 440 with cutting device 13, the sharp cutting edge 23 of legs 270, radio frequency generator 24, and/or emitter 25 is that in cases where the entrapped object may be too large for successful removal from the body, the entrapped object may be reduced in size and safely removed from the body.

Embodiments of the invention may be used in any medical or non-medical procedure wherein removal of an object from within a body lumen is desired. In addition, as least certain aspects of the aforementioned embodiments may be combined with other aspects of the embodiments, or removed, without departing from the scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a sheath having a proximal end and a distal end;
   a cutting device at the distal end of the sheath;
   a lumen extending longitudinally through both the sheath and the cutting device;
   an elongate member extending within the lumen and moveable relative to the sheath and the cutting device;
   a retrieval assembly connected to the elongate member and retractable within and extendable from the lumen of the sheath;
   wherein the distal end of the cutting device has an edge configured to cut an object entrapped in the retrieval assembly; and
   wherein the edge is curvilinear and the distal end of the cutting device includes a wall that tapers to the curvilinear edge.

2. The medical device of claim 1, wherein the cutting device is a hypotube having a sharp distal edge.

3. The medical device of claim 1, wherein the cutting device comprises a first material and the sheath comprises a second material different from the first material.

4. The medical device of claim 1, wherein an outer diameter of the cutting device is substantially constant; and
   wherein an inner diameter of the cutting device increases toward the edge.

5. The medical device of claim 1, wherein the distal end of the cutting device further comprises a cutting wire.

6. The medical device of claim 1, wherein the retrieval assembly comprises a plurality of legs.

7. The medical device of claim 6, wherein at least one of the plurality of legs comprises an inward facing sharp edge.

8. The medical device of claim 1, further comprising an energy generator configured to generate at least one of a RF energy, ultrasonic energy, and heat to a tissue sample positioned in the retrieval assembly.

9. A method of entrapping an object within a body, comprising:

inserting a medical device into a body lumen, the medical device comprising:
- a sheath having a proximal end and a distal end;
- a cutting device at the distal end of the sheath;
- a lumen extending longitudinally through both the sheath and the cutting device; an elongate member extending within the lumen and moveable relative to the sheath and cutting device; and
- a retrieval assembly connected to the elongate member and retractable within and extendable from the lumen of the sheath;

advancing the medical device to a site within the body lumen;

extending the elongate member and retrieval assembly distally relative to the sheath and cutting device to deploy the retrieval assembly; and entrapping the object within the retrieval assembly;

wherein the distal end of the cutting device has an edge configured to cut the portion of the object entrapped within the retrieval assembly; and wherein the edge is curvilinear and the distal end of the cutting device includes a wall that tapers to the curvilinear edge.

10. The method of claim 9, further comprising generating at least one of RF energy, ultrasonic energy, and heat to cut a portion of the object.

11. The method of claim 9, further comprising retracting the elongate member and retrieval assembly proximally relative to the sheath and cutting device after the step of entrapping the object within the retrieval assembly to cut a portion of the object.

12. The method of claim 9, further comprising rotating the elongate member and retrieval assembly relative to the cutting device while axially displacing the elongate member and the retrieval assembly relative to the cutting device.

13. The method of claim 9, wherein an outer diameter of the cutting device is substantially constant; and wherein an inner diameter of the cutting device increases toward the edge.

14. The method of claim 9, wherein the retrieval assembly comprises a plurality of legs; and wherein at least one of the plurality of legs comprises an inward facing sharp edge.

15. A method of cutting tissue from a tissue sample, comprising:

inserting a medical device into a body lumen, the medical device comprising:
- a device lumen having a distal end;
- a cutting device disposed at the distal end of the device lumen, wherein a distal end of the cutting device includes a cutting wire;
- an elongate member extending within and axially displaceable with respect to the device lumen; and
- a retrieval member disposed on a distal end of the elongate member; advancing the medical device to a site within the body lumen;

entrapping the tissue sample within the retrieval member; and axially displacing the elongate member and retrieval member relative to the cutting device to cut tissue from the tissue sample.

16. The medical device of claim 15, wherein the distal end of the cutting device has an edge configured to cut an object entrapped in the retrieval member; and wherein the edge is curvilinear and the distal end of the cutting device includes a wall that tapers to the curvilinear edge.

17. The medical device of claim 15, wherein the retrieval member comprises a plurality of legs; and wherein at least one of the plurality of legs comprises an inward facing sharp edge.

* * * * *